United States Patent
Watanabe et al.

(10) Patent No.: US 10,258,702 B2
(45) Date of Patent: Apr. 16, 2019

(54) METHOD FOR MANUFACTURING WATER-ABSORBENT CARRIER

(71) Applicant: TERUMO KABUSHIKI KAISHA, Tokyo (JP)

(72) Inventors: Eiji Watanabe, Kanagawa (JP); Yoshihiko Abe, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 421 days.

(21) Appl. No.: 15/082,671

(22) Filed: Mar. 28, 2016

(65) Prior Publication Data

US 2016/0206765 A1 Jul. 21, 2016

Related U.S. Application Data

(63) Continuation of application No. PCT/JP2014/075993, filed on Sep. 30, 2014.

(30) Foreign Application Priority Data

Sep. 30, 2013 (JP) .................. 2013-205357

(51) Int. Cl.
| | |
|---|---|
| *A61L 2/07* | (2006.01) |
| *B01J 20/18* | (2006.01) |
| *B01J 20/26* | (2006.01) |
| *B01J 20/32* | (2006.01) |
| *B01J 20/30* | (2006.01) |
| *B01J 20/10* | (2006.01) |
| *B01J 20/28* | (2006.01) |
| *A61J 1/10* | (2006.01) |

(52) U.S. Cl.
CPC .............. *A61L 2/07* (2013.01); *B01J 20/103* (2013.01); *B01J 20/18* (2013.01); *B01J 20/261* (2013.01); *B01J 20/262* (2013.01); *B01J 20/28026* (2013.01); *B01J 20/305* (2013.01); *B01J 20/3204* (2013.01); *B01J 20/327* (2013.01); *B01J 20/3272* (2013.01); *B01J 20/3293* (2013.01); *A61J 1/10* (2013.01)

(58) Field of Classification Search
CPC .. A61L 2/07; B01J 20/103; B01J 20/18; B01J 20/261; B01J 20/26
USPC ....................................... 502/402
See application file for complete search history.

(56) References Cited

U.S. PATENT DOCUMENTS

| | | |
|---|---|---|
| 5,432,214 A | 7/1995 | Lancesseur |
| 6,080,350 A | 6/2000 | Hekal |
| 2003/0034264 A1 | 2/2003 | Hamai et al. |

FOREIGN PATENT DOCUMENTS

| | | |
|---|---|---|
| JP | S55-151963 A | 11/1980 |
| JP | S59-041744 B2 | 10/1984 |
| JP | S60-066747 A | 4/1985 |
| JP | H05-014585 B2 | 2/1993 |
| JP | 2003-052819 A | 2/2003 |
| JP | 2006-063118 A | 3/2006 |
| JP | 2011-245734 | 12/2011 |

OTHER PUBLICATIONS

European Office Action dated May 25, 2018 in corresponding application No. 14849807.4.
Extended European Search Report dated May 2, 2017 in corresponding application No. 14849807.4.
Japanese Office Action dated Jun. 25, 2018 in corresponding application No. 2015-539447.
International Search Report for PCT/JP2014/075993 dated Jan. 13, 2015.

*Primary Examiner* — Edward M Johnson
(74) *Attorney, Agent, or Firm* — Foley & Lardner LLP

(57) ABSTRACT

A water-absorbent carrier for moist heat sterilization can be used in a narrow space and does not have a risk of generating foreign matter. The water-absorbent carrier is obtained by embedding a water-absorbent substance in a synthetic resin. The water-absorbent carrier can be manufactured by impregnating the water-absorbent substance with a water-soluble substance, drying the water-absorbent substance, embedding the water-absorbent substance in a thermoplastic synthetic resin, and washing the water-absorbent substance to remove the water-soluble substance. Alternatively, the water-absorbent carrier can be manufactured by dispersing a water-insoluble synthetic resin in a dispersion medium, mixing the water-absorbent substance in the dispersion medium, pouring the mixture into a mold, and volatilizing the dispersion medium. A medical article to be sterilized includes the water-absorbent carrier packaged in a closed space. Moist heat sterilization (autoclave sterilization) of the medical article can be performed at a moist heat temperature exceeding 100° C.

2 Claims, 2 Drawing Sheets

METHOD FOR MANUFACTURING WATER-ABSORBENT CARRIER

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2014/075993 filed on Sep. 30, 2014, which claims priority to Japanese Patent Application No. 2013-205357, filed on Sep. 30, 2013. The contents of these applications are hereby incorporated by reference in their entireties.

BACKGROUND

The present invention relates to a water-absorbent carrier, a method for manufacturing the water-absorbent carrier, a medical article packaged with the water-absorbent carrier in a space to be sterilized, and a moist heat sterilization method. The water-absorbent carrier is provided in a part over which water vapor cannot readily spread during the moist heat sterilization.

Conventionally, it is known as a rule of thumb that spore bacteria can survive in a dry condition even at a high temperature of, for example, 121° C. Therefore, a moist heat sterilization method has been employed for the purpose of sterilizing a part not containing water within a packaging bag for a medical article to be sterilized in such a way that a nonwoven fabric or the like having a good water vapor transmittance is used as at least a part of the packaging bag to introduce water vapor that serves as a sterilant.

During the moist heat sterilization, water vapor denatures a protein component and a nucleic acid structure of a microorganism, thereby killing the microorganism. Therefore, a technique for spreading heated water vapor over a part to be sterilized has been required. As mentioned above, water vapor functions as a sterilant for the moist heat sterilization. In particular, it can be said that saturated water vapor functions as a sterilant for moist heat sterilization (autoclave sterilization).

However, such a conventional packaging bag suffers from propagation of mold or the like due to damage to the nonwoven fabric and insufficient drying after sterilization. Therefore, it has been necessary to dry the packaging bag including the inside thereof for a certain period of time after the sterilization process.

In JP 59-041744 B ("Patent Literature 1"), a "medical item packaging body" has been proposed as a means to solve this problem. Specifically, a medical article is packaged in an airtight manner using a flexible material which does not substantially transmit water vapor (e.g. polypropylene, polyethylene, nylon, polyester, polyvinyl chloride, or a laminated body including other synthetic resins), and a water-absorbent body (filter paper) preliminarily containing water is contained in the package.

JP 05-014585 B ("Patent Literature 2") has introduced a "heating sterilization method for a container". Specifically, a container is closely packaged in an exterior body together with silica gel into which water is absorbed or on which water is carried. The exterior body is then heated for a certain period of time at a temperature of 50° C. or higher, and naturally cooled at room temperature. In Patent Literature 2, more specifically, silica gel into which water is absorbed or on which water is carried is put in a bag made of polyethylene, and an opening of the bag is sealed with a rubber band, and closely packaged in the exterior body together with an object to be sterilized (container). The exterior body is then heated for a certain period of time at a temperature of 50° C. or higher, and left to cool at room temperature.

Furthermore, JP 2003-052819 A ("Patent Literature 3") has proposed a "package for an injector filled with a medicine and sterilization of the same or a sterilization method therefore". Specifically, a prefilled syringe is vacuum-packaged and sterilized in order to prevent water from remaining in a cap or a nozzle when sterilizing the prefilled syringe. In Patent Literature 3, it is described that a temperature sensor placed in a syringe body indicates a temperature of 121° C.

SUMMARY

However, although the above-mentioned technique of Patent Literature 1 has enabled sterilization using a water-absorbent body (filter paper), the water-absorbent body might generate foreign matter such as fiber dust since the water-absorbent body itself is a fiber product. Since the generation of foreign matter might impede functionality of a medical article (e.g. blood vessel catheter), the technique of Patent Literature 1 has not been widely used. In particular, in order to arrange the water-absorbent body (filter paper) so as to allow water vapor to spread over a narrow space, the filter paper needs to be made small. It is not preferable to cut the filter paper for this purpose since a cut end might create much more fiber dust.

In addition, since water absorbency of a fiber product is inferior to that of silica gel or zeolite, which are capable of absorbing water even at a relative humidity of 30% RH or less, the humidity inside the package becomes 50% RH or more. Accordingly, rust might be generated on a metal surface, and water cannot be removed from powder having a critical humidity of 50% RH or less.

In the above-mentioned technique of Patent Literature 2, silica gel is put in a bag made of polyethylene, and an opening of the bag is sealed with a rubber band in order to solve the above-mentioned disadvantage of Patent Literature 1, namely the generation of foreign matter.

However, putting silica gel in the bag made of polyethylene makes it difficult to be used in a narrow space. In addition, it is known that if granules of silica gel themselves are packaged together with a medical article and heated, the granules of silica gel are fractured and micronized into small pieces while they are heated. Such micronized small pieces are contained in the medical article and formed into foreign matter that looks like small pieces of glass. Such a medical article is not suitable for being embedded in a human body or being joined to another medical article since the foreign matter might also be mixed in the human body or the medical article. This technique also cannot be used for friction surfaces since fine powder invades the friction surfaces. Usage of this technique is therefore limited.

Furthermore, a heating temperature described in Patent Literature 2 is 50° C. or higher, and does not reach 100° C. or higher at which spore-forming bacteria can be sterilized. Therefore, the technique of Patent Literature 2 cannot be applied to the medical article.

The above-mentioned Patent Literature 3 is a technique for preventing water from remaining in a cap or a nozzle of a prefilled syringe, and does not clarify whether a sterilant (saturated vapor) containing water that is required for moist heat sterilization (autoclave sterilization) has reached the cap or the nozzle. Generally, as mentioned above, it is known as a rule of thumb that spore bacteria can survive in a dry condition at 121° C. Therefore, Patent Literature 3 has a risk of existence of spore bacteria.

For example, in a case where moist heat sterilization is used for sterilizing a blood vessel catheter capable of running through a blood vessel owing to its moist condition, it has been difficult to allow vapor to reach every part inside the catheter since in many cases such a catheter exceeds 2 m. In addition, in a case where silica gel or the like is disposed between the catheter and a cover thereof, the silica gel remains on the catheter at the point of use to be formed into foreign matter, and the foreign matter might further cause a delay in movement of the catheter, which is why the silica gel or the like has not been able to be used.

It is a problem of the present invention to provide a water-absorbent carrier for moist heat sterilization which can be used even in a narrow space, does not generate foreign matter, and does not deteriorate a function of a medical article, a method for manufacturing the water-absorbent carrier, the medical article, and a moist heat sterilization method.

The present inventors have intensively studied to solve the above-mentioned problem, and found that this problem can be solved by using a water-absorbent carrier obtained by embedding a water-absorbent substance (e.g. silica gel, zeolite, or polyacrylic acid) in a synthetic resin (e.g. low-molecular polyethylene or silicone resin). Specifically, such an amount of water that can be subjected to moist heat sterilization is preliminarily held by the water-absorbent substance, and the water-absorbent carrier is put in a space that vapor cannot readily enter.

In other words, the water-absorbent carrier is arranged in a moist heat sterilization (autoclave sterilization) machine or a sealed space, and heated by heat, an electron beam or the like to generate vapor. As a result, an area that vapor from the outside cannot readily enter is subjected to the moist heat sterilization and becomes an aseptic environment. When the aseptic environment is cooled, water is absorbed into the support again. Since the environment is kept aseptic and not exposed to water, rust is not generated even in a case where a structure to be sterilized is made of metal. Even if dried powder exists between adjacent partition walls, the dried powder is free from deterioration due to an influence of water. In addition, since the water-absorbent carrier can be a molded product, the water-absorbent carrier can be incorporated as a single component depending on a shape at the time of manufacture.

A method for manufacturing the water-absorbent carrier includes two methods. In one method, the water-absorbent carrier can be manufactured by impregnating a water-absorbent substance with a water-soluble substance, drying the water-absorbent substance, embedding the water-absorbent substance in a thermoplastic synthetic resin, and washing the water-absorbent substance to remove the water-soluble substance (first manufacturing method). In the other method, the water-absorbent carrier can be manufactured by dispersing a synthetic resin (dispersion medium dilution type silicone resin and acrylic resin are suitable) in a dispersion medium, mixing a water-absorbent substance therein, and volatilizing the dispersion medium (second manufacturing method).

More specifically, the present invention is what is described in the following (1) to (13).

(1) A water-absorbent carrier for moist heat sterilization obtained by embedding a water-absorbent substance in a synthetic resin.
(2) The water-absorbent carrier according to the above-mentioned (1),
wherein the water-absorbent substance is a substance that absorbs water at room temperature ranging from 1 to 30° C., releases the water when heated, and does not decompose at 121° C.
(3) The water-absorbent carrier according to the above-mentioned (2),
wherein the water-absorbent substance is any one of silica gel, zeolite, and polyacrylic acid.
(4) The water-absorbent support according to any of the above-mentioned (1) to (3),
wherein a void is provided between the synthetic resin and the water-absorbent substance embedded in the synthetic resin.
(5) A method for manufacturing a water-absorbent carrier, including:
an immersing step of immersing a water-absorbent substance in an aqueous solution in which a water-soluble substance is dissolved;
a drying step of drying the water-soluble substance carried on the water-absorbent substance in the immersing step;
an embedding step of embedding, in a thermoplastic synthetic resin, the water-absorbent substance carrying the water-soluble substance dried during the drying step; and
a washing step of washing a molded body obtained in the embedding step to remove the water-soluble substance.
(6) The method for manufacturing a water-absorbent carrier according to the above-mentioned (5), wherein
the embedding in the thermoplastic synthetic resin in the embedding step is performed in such a way that while the thermoplastic synthetic resin is heated and dissolved, the thermoplastic synthetic resin is mixed with the water-absorbent substance, and then cooled.
(7) A method for manufacturing a water-absorbent carrier, including:
a dispersion or dissolution liquid preparing step of dispersing or dissolving a synthetic resin in a dispersion medium or a solvent;
a mixing step of mixing a water-absorbent substance in the dispersion liquid or the dissolution liquid; and
a molding step of volatilizing the dispersion medium or the solvent from a mixture obtained in the mixing step.
(8) A medical article, wherein
the water-absorbent carrier according to any of the above-mentioned (1) to (4) is arranged in a bag-shaped container.
(9) The medical article according to the above-mentioned (8), wherein
the water-absorbent carrier on which water is carried is arranged in a region that water vapor for moist heat sterilization cannot readily reach.
(10) A sterilization method for a medical article, wherein
moist heat sterilization is performed by arranging the water-absorbent carrier according to any of the above-mentioned (1) to (4) in a region of an object to be sterilized that water vapor cannot readily reach.
(11) A sterilization method for a medical article, wherein
moist heat sterilization is performed by arranging the water-absorbent carrier according to any of the above-mentioned (1) to (4) in a bag-shaped container for an object to be sterilized.
(12) A sterilization method for a medical article, wherein
moist heat sterilization is performed by arranging the water-absorbent carrier according to any of the above-mentioned (1) to (4) in a region within a moist heat sterilization apparatus that water vapor cannot readily reach.
(13) The sterilization method according to any of the above-mentioned (10) to (12), wherein the moist heat sterilization is moist heat sterilization (autoclave sterilization).

According to the present invention, it is possible to provide a water-absorbent carrier for moist heat sterilization which can be used even in a narrow space, does not generate foreign matter, and does not deteriorate a function of a medical article, a method for manufacturing the water-absorbent carrier, the medical article, and a moist heat sterilization method.

DETAILED DESCRIPTION

Figures 1A, 1B, 1C, 1D, 1E:
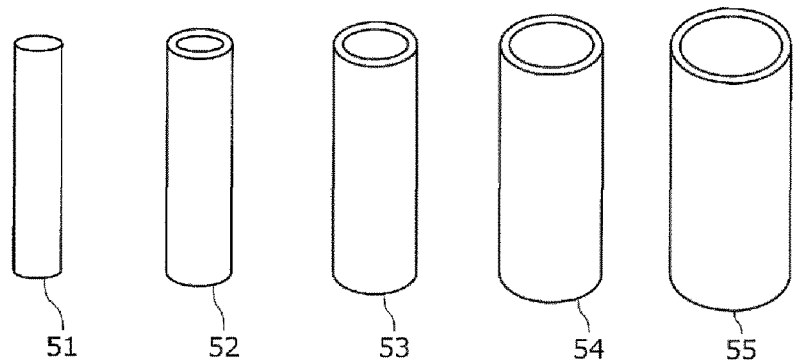
FIGS. 1A to 1F are views illustrating an example of using a water-absorbent carrier for a bearing of an arm of a surgery robot (Example 5).

<<Description of Terms and Concepts Used in Specification>>

Spore bacteria are bacteria that form a cell structure having extremely high durability. Spores have extremely strong resistance to high temperatures in comparison with common bacteria. The spores are also resistant to boiling disinfection at 100° C., and further resistant to chemical substances such as common disinfectants.

Moist heat sterilization generally refers to a sterilization method that uses water vapor at a high temperature as a sterilant. Moist heat sterilization refers to heat sterilization which is carried out in saturated water vapor at 121° C. and 2 atm for 15 minutes or longer (typically 20 minutes). An autoclave apparatus is generally an apparatus which is used for the moist heat sterilization.

Sterilization refers to killing off or removing all microorganisms from a substance. An aseptic assurance level is represented by a probability that a single microorganism exists in a sterilized product (probability of one over 10 to the n-th power). For example, the aseptic property is assured at a level of $10^{-6}$, in other words, when the existence probability of bacteria is one over $10^6$.

A medical article is a term that includes, for example, various types of medical devices, combinations of medical devices and medicines, containers for medical devices or containers for medicines, and containers in which medical devices or medicines are contained. In other words, the medical article is a term that broadly encompasses items which are used for medical purposes (refer to <<Objects to be Sterilized>> described later).

A water-absorbent carrier is used for the purpose of spreading water vapor during the moist heat sterilization, and obtained by embedding a water-absorbent substance in a synthetic resin. Since the water-absorbent substance is embedded in the synthetic resin, the water-absorbent substance is hardly broken even by mechanical external force. The water-absorbent substance embedded in the synthetic resin has a characteristic of absorbing water at a temperature ranging from 1 to 30° C., and releasing the water when heated. Although the water-absorbent substance is embedded in the synthetic resin, a passage is provided for allowing water molecules (e.g. monomer to pentamer or the like) to pass therethrough between the internal water-absorbent substance and the outside thereof.

Embedding refers to burying something in something else. In the present invention, "embedding" refers to surrounding the water-absorbent substance using the synthetic resin in order to prevent the water-absorbent substance from being broken by mechanical force or the like from the surroundings. In this regard, the passage for a low-molecular compound having a molecular weight of 1000 or less water and water vapor is secured so as not to inhibit a water-absorbing property of the water-absorbent substance.

A void is provided between the synthetic resin and the embedded water-absorbent substance, or provided in the synthetic resin to form the passage for the low molecule compound having a molecular weight of 1000 or less water and water vapor. The void has such a size that water, a low-molecular compound having a molecular weight of 1000 or less or the like, can freely pass through the void.

The water-absorbent substance (e.g. silica gel, zeolite, polyacrylic acid or the like) is generally available in the form of granules. However, the granules themselves might be deformed due to mechanical force, heat or the like, resulting in occurrence of failure. Therefore, the granules shall be embedded in the synthetic resin to be protected from force, heat or the like.

In addition, even while the water-absorbent substance is embedded, the water-absorbent substance retains its water-absorbing property, and exhibits the characteristic of absorbing water at room temperature and releasing the water when heated. By using the water-absorbent carrier obtained by embedding the water-absorbent substance in the synthetic resin as mentioned above, water vapor that serves as a sterilant for the moist heat sterilization can reach an object to be sterilized even in a narrow space. It is preferable that at least a portion of the released water is absorbed again into the water-absorbent substance at a point of time when the temperature is returned to room temperature after the sterilization of the object.

<<Objects to be Sterilized>>

Examples of the objects to be sterilized in the present invention can include various types of medical devices such as syringes (including single-chamber or multiple-chamber prefilled syringes), injection needles, scalpels, scissors, blood vessel catheters, infusion tubes, infusion three-way stopcocks, electric scalpels, and surgery robots. Further examples of the objects to be sterilized in the present invention can include combinations of medical tools and medicines, e.g. single-chamber or multiple-chamber prefilled syringes, medicine administration tools or the like, containers for medical devices or containers for medicines formed in a bag, tubular, or cuboid shape, and containers in which medical devices or medicines are contained. The water-absorbent carrier of the present invention is applied to a part of any of these objects that vapor especially cannot readily enter during the moist heat sterilization.

<<Specific Examples of Water-Absorbent Substances and Synthetic Resins>>

The water-absorbent substance that is used in the present invention includes, but is not limited to, silica gel, zeolite, polyacrylic acid or the like. Any substance can be used as long as it absorbs water at a temperature ranging from 1 to 30° C., releases the water when heated, and does not get damaged at 121° C. There is no particular restriction on a granule diameter as long as it is such a diameter that the granules can be embedded in the molded synthetic resin. With regard to silica gel, for example, silica gel granules having a diameter of 2 to 20 µm are generally commercially available for the purpose of chromatography, and silica gel granules having a diameter of 0.3 to 5 mm are also generally commercially available as desiccants. Both of them can be used in the present invention.

The synthetic resin that is used in the present invention includes various types of hard plastic materials and various types of soft plastic. Preferable examples of the hard plastic materials include polypropylene, polyethylene, poly(4-methylpentene-1), polyolefin such as cyclic polyolefin, polyethylene terephthalate, polyethylene naphthalate, polyester such as amorphous polyarylate, polystyrene, polyamide, polycarbonate, polyvinyl chloride, acrylic resin, acrylonitrile-butadiene-styrene copolymer, and amorphous polyetherimide or the like. Particularly preferable examples of the hard plastic materials include polypropylene, poly(4-methylpentene-1), cyclic polyolefin, polyethylene naphthalate, and amorphous polyetherimide or the like. Examples of the soft plastic include thermoplastic elastomer, soft silicone resin, low-density polyethylene, polyethylene-vinyl acetate copolymer, and soft polyvinyl chloride resin or the like. Among these synthetic resins, polyethylene, polypropylene, and silicone resin or the like are resins which are suitable for preparing the water-absorbent carrier of the present invention using a thermoforming method. In addition, methyl acrylate resin, vinyl acetate resin, urethane resin, polyamide including nylon, and polyvinylidene fluoride or the like are resins which are suitable for preparing the water-absorbent carrier of the present invention by dissolving or dispersing the resin in a solvent (solvent or dispersion medium) such as an organic solvent or water.

A water-soluble substance is a water-soluble low-molecular solid substance such as D-mannitol or sodium chloride. The water-soluble substance can infiltrate a porous water-absorbing structure of the water-absorbent substance so that the water-absorbent substance is impregnated with the water-soluble substance. A variety of substances including saccharides and salts or the like can be used as long as the substance can infiltrate a porous structure of silica gel or zeolite so that silica gel or zeolite is impregnated with the substance, and the substance is dried and solidified. In a case where the water-soluble substance is used in the thermoforming method, it is preferable that the water-soluble substance does not melt at a thermoforming temperature of the thermoforming method. For example, it is preferable to use anhydrous glucose since it does not melt until it reaches 146° C.

<<First Manufacturing Method for Water-Absorbent Carrier>>

The water-absorbent carrier of the present invention is such a carrier that the water-absorbent substance is embedded in the synthetic resin. A method for manufacturing the water-absorbent carrier differs depending on the synthetic resin. Generally, the water-absorbent carrier can be prepared by using a method for molding a resin.

First, the manufacturing method for melting the synthetic resin which is a thermoplastic resin in which the water-absorbent substance will be embedded is described.

The manufacturing method includes four steps as follows:
(1) an impregnating step of immersing a water-absorbent substance in an aqueous solution in which a water-soluble substance is dissolved to impregnate the water-absorbent substance with the water-soluble substance;
(2) a drying step of drying the water-absorbent substance impregnated with the water-soluble substance in the impregnating step;
(3) an embedding step of embedding, in a thermoplastic synthetic resin, the water-absorbent substance dried during the drying step; and
(4) a washing step of washing a molded body obtained in the embedding step to remove the water-soluble substance.

Furthermore, the manufacturing method is made available with the addition of:
(5) a water carrying step of supplying water for sterilization, at the same time as or after the washing step, to the water-absorbent substance configured to absorb water such that the water for sterilization is carried on the water-absorbent substance. In a case where the water-absorbent carrier is not immediately used, after the washing step, the molded body is dried and stored. After that, the molded body is subjected to the water carrying step before use to be made available.

The "immersing" in the immersing step refers to soaking something in something else. Specifically, the immersing step is a step of soaking the water-absorbent substance in the aqueous solution to allow the water-soluble substance to permeate through openings in the porous structure of the water-absorbent substance. In this case, the water-soluble substance (e.g. D-mannitol and sodium chloride or the like) is allowed to permeate through the water-absorbent substance by mixing the water-soluble substance with the water-absorbent substance in the aqueous solution at normal room temperature and 1 atm.

The drying in the drying step may be, for example, natural drying, which is performed in such a way that the substance is left as it is for 24 hours. Alternatively, the substance may be heated and forcibly dried. For example, the water-absorbent substance impregnated with the water-soluble substance can be placed in a sieve made of stainless steel, and exposed to hot air at about 100° C. to be dried.

The embedding in the embedding step is enabled by a method similar to a method for molding a resin using a thermoplastic synthetic resin. The thermoplastic synthetic resin is dissolved in a silicone oil bath at, for example, 150° C. The water-absorbent substance dried in the drying step is mixed in the dissolved thermoplastic synthetic resin. Such a mixed resin is sandwiched between, for example, two stainless steel plates and held so as to be formed into a sheet having a thickness of 3 mm. After that, the sheet is left as it is at room temperature, whereby the resin is cooled and solidified. Thus, the water-absorbent substance is embedded in the resin.

The washing step is performed by washing with water.

The water-absorbent carrier obtained in the above-mentioned method maintains its water-absorbing property, namely the characteristic of absorbing water at a temperature ranging from 1 to 30° C. and releasing the water when heated.

It is considered that the water-soluble substance is attached to a part that serves as the passage through which the water-absorbent substance absorbs or discharges water, so that the thermoplastic synthetic resin is prevented from blocking the passage. After embedding the water-absorbent substance in the thermoplastic synthetic resin, the water-soluble substance can be washed to be removed. As a result, the passage for water molecules of the water-absorbent substance is formed.

As a high-molecular compound that serves as the thermoplastic synthetic resin suitable for this first manufacturing method, the resins such as polyethylene and polypropylene are preferably used since they are generally supplied in the form of pellets and melted when heated.

The water-absorbent carrier that is obtained using this first manufacturing method is formed in a granular shape (second production example to be described later) or a sheet shape (first production example to be described later). During or after the above-mentioned washing step, the water-absorbent substance is allowed to contain water to become the carrier into which the water is absorbed.

<<Second Manufacturing Method for Water-Absorbent Carrier>>

Second, the synthetic resin which is manufactured by evaporating and hardening the dispersion medium can in many cases create therein a space that exhibits the water-absorbing property since the volume is reduced due to evaporation of a dispersion liquid. Therefore, such a synthetic resin does not require the operation for preliminarily attaching the water-soluble substance. A solvent dilution type silicone resin, acrylic resin, and urethane resin or the like are preferably used.

The dispersion as used herein refers to a state where a liquid dispersoid and a liquid dispersion medium are mixed and suspended. An example of a silicone elastomer is a two-agent reaction type silicone which is obtained in such a way that a raw material including two agents is mixed, when used, in a dispersion medium so as to be reacted and hardened. An example of the raw material including two agents is a raw material including a reactive silicone resin and a crosslinking agent such as a silane coupling agent. Another example of the silicone elastomer is obtained in such a way that both of the reactive silicone resin and the crosslinking agent are used as dispersoids, and toluene is used as the dispersion medium so that a 10% toluene dispersion liquid is prepared. After this dispersion liquid is prepared, the toluene serving as the dispersion medium is volatilized. As a result, the silicone resin is solidified to become the silicone elastomer. Although the dispersoid has been assumed to be a liquid in the above-mentioned explanation, the dispersoid is not limited to a liquid in the present invention.

Such a resin is referred to as a "solvent dilution type resin". Strictly speaking, however, the toluene in this example is not a solvent but a dispersion medium. The second manufacturing method can be similarly applied to, in addition to the above-mentioned synthetic resin which is manufactured by evaporating and hardening the dispersion medium, a synthetic resin which is manufactured by evaporating and hardening a solvent. Such a synthetic resin is, in other words, dissolved in a solvent and classified as the "solvent dilution type resin" defined in the strict sense.

The second manufacturing method includes three steps as follows.

The three steps include:
(1) a dispersion liquid preparing step of dispersing a synthetic resin (solvent dilution type resin) in a dispersion medium;
(2) a mixing step of mixing a water-absorbent substance in the dispersion liquid; and
(3) a molding step of volatilizing the dispersion medium from a mixture obtained in the mixing step.

Among these steps, the dispersion liquid preparing step differs depending on each solvent dilution type resin. Therefore, the dispersion liquid needs to be prepared according to an instruction manual provided by a manufacturer of each solvent dilution type resin.

The mixing in the mixing step is performed by, for example, agitating the mixture so that the mixture can be uniformly mixed.

The molding step is a step of volatilizing the dispersion medium by leaving the mixture as it is. The volatilized mixture is molded to a shape conforming to a container in which the mixture has been contained. For example, in a case where the mixture is put in a tray, the mixture is molded to a sheet shape having a substantially uniform thickness. Therefore, the mixture can be molded to a desired shape by selecting the container for the mixture.

By using this feature, the water-absorbent carrier can be manufactured as a thin film (sheet shape) having a thickness of 5 mm. The obtained sheet-shaped water-absorbent carrier can be cut into a desired shape. Alternatively, a desired shape can be obtained by preparing a desired mold, pouring the above-mentioned mixture into the desired mold, and volatilizing the dispersion medium. In that sense, it can be said that the water-absorbent carrier can be produced as a molded product.

The water-absorbent carrier which is manufactured using the second manufacturing method also has the above-mentioned water-absorbing property (characteristic of absorbing water at a temperature ranging from 1 to 30° C. and releasing the water when heated).

As the result of the volatilization of the dispersion medium, the passage for water molecules of the water-absorbent substance is formed. In other words, the function of the water-soluble substance in the first manufacturing method is performed by the dispersion medium in the second manufacturing method.

<<Function of Water-Absorbent Carrier>>

The water-absorbent carrier of the present invention is characterized in that its water-absorbing power is weakened by heat. Therefore, the water-absorbent carrier of the present invention can release water when heated and perform sterilization in a moist heat atmosphere. In addition, since the water-absorbing power of the water-absorbent carrier is recovered when cooled, the water-absorbent carrier is enabled to absorb the released water. Therefore, it is possible to prevent a risk that an object to be sterilized may be adversely affected by excess water at room temperature.

<<Storage of Water-Absorbent Carrier>>

The carrier obtained by embedding the above-mentioned water-absorbent substance in the synthetic resin is stored in a dry condition. The carrier can be put in boiling water immediately before it is used as the water-absorbent carrier for the sterilization, and then cooled to carry water. It is desirable that the water-absorbent carrier is used quickly once it carries water in order to prevent propagation of mold or the like. The water-absorbent carrier and water are put in a closely sealed bag to be subjected to the moist heat sterilization. The bag is then stored and kept closed until use. This method is advantageous in that inconvenience from generation of mold or the like can be avoided, and is convenient in that the water-absorbent carrier can be made immediately available.

<<Use of Water-Absorbent Carrier for Medical Article>>

The water-absorbent carrier is appropriately used for, for example, the above-mentioned various types of medical devices, combinations of medical devices and medicines, containers for medical devices or containers for medicines. In other words, the water-absorbent carrier is appropriately used for items which are utilized for medical purposes. Specifically, the water-absorbent carrier is arranged and used in a part of any of these items that vapor cannot readily enter during the moist heat sterilization. The containers in which medical devices or medicines are contained are subjected to the autoclave sterilization again as needed.

<<Sterilization Method Using Water-Absorbent Carrier>>

Water carried on the water-absorbent carrier functions as a sterilant for the moist heat sterilization. As the temperature is lowered after the sterilization is completed, the water is absorbed into the water-absorbent carrier again.

A particular variation of the moist heat sterilization method is referred to as the moist heat sterilization. The moist heat sterilization is performed under a condition of 121° C., 2 atm, and 15 minutes or longer in saturated water vapor. Moist heat (hot water and water vapor) serves as a sterilant for the moist heat sterilization. Water carried on the water-absorbent carrier functions as a sterilant for the moist heat sterilization as well. As the temperature is lowered after the sterilization is completed, the water is absorbed into the water-absorbent carrier again.

Next, the present invention will be described further in detail with reference to Examples and test examples. The present invention is not limited to these Examples and test examples.

EXAMPLE 1

First Production Example of Water-Absorbent Carrier According to First Manufacturing Method Example 1 shows a first production example obtained by producing the water-absorbent carrier using the above-mentioned first manufacturing method.

The following materials were used:
water-absorbent substance: zeolite, Molecular Sieves 3A 1/16 (Nacalai Tesque);
synthetic resin: low-molecular polyethylene: Novatec LD Grade LJ802 (melting point (DSC measurement): 106° C.) (Japan Polyethylene); and
water-soluble compound: D-mannitol (Roquette Corp.).

In a 100 mL beaker, 10 g of zeolite and 50 mL of a 20% mannitol aqueous solution were mixed and placed in a stainless steel basket to be dried at 100° C. Meanwhile, 10 g of polyethylene were placed in a glass beaker, and dissolved in a silicone oil bath at 150° C. Five grams of the foregoing dried zeolite powder were placed in the dissolved polyethylene and stirred, taken out of the oil bath, placed on a stainless steel plate having a thickness of 3 mm, covered with another stainless steel plate so as to be sandwiched between the stainless steel plates, and held at a thickness of 3 mm. The obtained sheet was cooled and solidified.

The sheet was soaked in water for injection, placed in a 100 mL glass beaker and directly subjected to the autoclave process at 121° C. for 60 minutes so that mannitol was eluted with water for injection. After cooling, the sheet was washed with water for injection to obtain a water-absorbent carrier on which water is carried.

EXAMPLE 2

Second Production Example of Water-Absorbent Carrier According to First Manufacturing Method Example 2 shows a second production example obtained by producing the water-absorbent carrier using the above-mentioned first manufacturing method.

The following materials were used:
water-absorbent substance: silica gel 60HF with a granule diameter or about 2 μm to 20 μm (Nacalai Tesque, Inc.);
synthetic resin: silicone elastomer: Medical Grade Elastomer Base MDX4-4210 (Dow Corning Corp.) which is a two-agent reaction type silicone including a reactive silicone resin which is itself a liquid and a crosslinking agent which is a silane coupling agent, respectively; and
water-soluble compound: sodium chloride, Japanese Pharmacopoeia sodium chloride (Tomita Pharmaceutical Co., Ltd.).

In a 100 mL beaker, 10 g of silica gel and 5 g of sodium chloride were mixed, and 50 mL of water were added in the beaker to dissolve the sodium chloride. The mixture was then dried at 100° C. Silicone elastomer was selected as the synthetic resin. In particular, reactive silicone resin and a crosslinking agent, which is the silane coupling agent of Medical Grade Elastomer Base MDX4-4210, were mixed at a ratio of 10:1. After that, before the synthetic resin was solidified, 1 pts.wt. of the above-mentioned dried substance were mixed in 3 pts.wt. of the synthetic resin (ratio of 1:3) to produce a droplet of about 3 mm on a stainless steel plate using a dropper. The droplet was subjected to a crosslinking process at 60° C. for 1 hour to obtain a silicone elastomer granule. The produced silicone elastomer granule was placed in a 100 mL beaker. Water for injection was added in the beaker and directly boiled for 60 minutes or subjected to the autoclave process at 121° C. for 60 minutes so that the sodium chloride could be easily removed when washed. After cooling, the granule was further washed with water for injection, and the sodium chloride was removed to obtain a water-absorbent carrier on which water is carried.

EXAMPLE 3

Third Production Example of Water-Absorbent Carrier According to Second Manufacturing Method Example 3 shows a third production example obtained by producing the water-absorbent carrier using the above-mentioned second manufacturing method.

The following materials were used:
water-absorbent substance: zeolite 4A (Tosoh Corporation); and
synthetic resin: silicone elastomer, 10% toluene dispersion liquid of 1:1 mixture of A component and B component of Medical Grade ETR Elastomer Q7-4750 (Dow Corning Corp.)

The synthetic resin and the water-absorbent substance were mixed such that the synthetic resin was 4 pts.wt., expressed in terms of dried weight, to 1 pts.wt. of the water-absorbent substance in a dry condition. The mixture was then put in a tray, and toluene serving as the dispersion medium was volatilized to produce a thin film of 5 mm.

The thin film of 5 mm was cut into a sheet shape of 5 cm×5 cm, put in boiling water for 5 minutes, and cooled as it was to obtain a sheet-shaped water-absorbent carrier on which water is carried.

EXAMPLE 4

Example of Using Water-Absorbent Carrier for Syringe (Test Example)

Example 4 is an example of using the water-absorbent carrier for a syringe, and also provides a test example to show sterilization effects of the above-mentioned second production example and third production example of the water-absorbent carrier.

The test was conducted by subjecting an object to be sterilized to the moist heat sterilization. A syringe made of glass having a capacity of 10 mL with an injection needle attached to a nozzle of the syringe was selected as the object to be sterilized. A single silicone elastomer granule containing the silica gel (second production example) produced in Example 2 was put in a protector which is a rubber cap made of butyl rubber. In addition, the sheet (third production example) produced in Example 3 was cut into a size of 2 cm×5 cm and put in a polypropylene outer bag for sterilization. In addition, a filter paper to which $10^6$ CFU/support of *Geobacillus stearothermophilus* was attached was put in the rubber cap and prepared as a biological indicator (hereinafter referred to as BI). The injection needle was then mounted on the nozzle of the syringe and covered with the rubber cap, whereby a syringe barrel assembly was assembled. The assembled syringe barrel was set and put in the outer bag, an opening of which was closely sealed using a heat-sealing process. This outer bag was sterilized at 121° C. for 20 minutes using an autoclave manufactured by Tomy Digital Biology Co., Ltd. The sterilized outer bag was opened in a clean bench, and the BI was taken out of the outer bag. The BI was then put in a SCD liquid medium to be cultured at 55 to 60° C. for 7 days. As a result, the culture solution did not become turbid, which proved that the sterilization was successfully performed.

The BI as used herein stands for the biological indicator, namely a bioindicator, which is used for a sterilization assurance of moist heat sterilization (autoclave sterilization). An ISO standard specifies that an initial number of bacteria of the BI used in a validation study is $10^6$ CFU/support. The CFU stands for a colony forming unit, which is a unit for measuring the amount of bacteria.

EXAMPLE 5

Example of Using Water-Absorbent Carrier for Bearing of Arm of Surgery Robot (Test Example)

Example 5 is an example of using the water-absorbent carrier for a bearing of an arm of a surgery robot, and also provides a test example to show a sterilization effect of the above-mentioned third production example of the water-absorbent carrier.

First, as illustrated in FIGS. 1A to 1E, a first shaft 51 and a second shaft 55 made of SUS316 stainless steel and a first spacer 52 and a second spacer 54 made of a fluororesin were prepared. A water-absorbent carrier 53 was manufactured in the method of Example 3 using polypropylene and zeolite. Specifically, the water-absorbent carrier (third production example) produced in the method of Example 3 has a sheet shape, which was cut into a desired size. Left and right ends of the obtained cut sheet were connected to each other to obtain the sheet in a cylindrical shape. The water-absorbent carrier in such a cylindrical shape was used in Example 5.

Figure 1F:
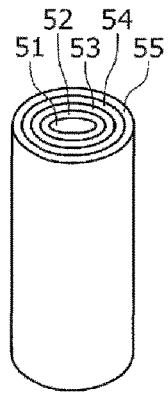
Figures 2A, 2B, 2C, 2D:
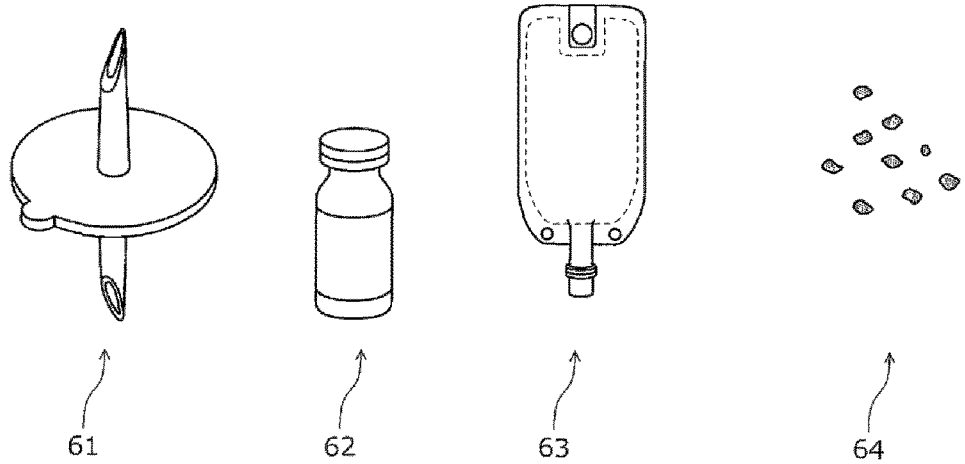
FIGS. 2A to 2D are views illustrating members associated with a medicine administration tool (Example 6).

As illustrated in FIG. 1F, the bearing has such a nesting structure that the first shaft 51 positioned at the very center of the bearing is surrounded by the first spacer 52, the water-absorbent carrier 53 according to the present invention around the first spacer 52, the second spacer 54 around the water-absorbent carrier 53, and the second shaft 55 provided on the outermost side of the bearing.

In order to prepare a comparative example, the same material as the spacers 52 and 54 was formed in the same shape as the water-absorbent carrier 53 such that a missing portion was provided in a part of a circumference portion. A filter paper to which $10^6$ CFU/support of *Geobacillus stearothermophilus* was attached was put as the biological indicator in the missing portion, and the obtained sheet was assembled to be used in place of the water-absorbent carrier 53 of Example 5, whereby a bearing was produced.

Such a bearing was wrapped in a sterilization bag made of a single-side nonwoven fabric, and sterilized at 121° C. for 15 minutes using the autoclave manufactured by Tomy Digital Biology Co., Ltd. The sterilized outer bag was opened in a clean bench, and the BI was taken out of the outer bag. The BI was then put in a SCD liquid medium to be cultured at 55 to 60° C. for 7 days. As a result, the culture solution for the bearing of Example 5 did not become turbid, which proved that the sterilization was successfully performed.

On the other hand, as the comparative example, the bearing without the water-absorbent carrier was sterilized in the same way. As a result, the culture solution was turbid, and surviving bacteria were observed, which revealed that the sterilization was not sufficient.

EXAMPLE 6

Example of Using Water-Absorbent Carrier for Medicine Administration Tool (Test Example)

Example 6 is an example of using the water-absorbent carrier for a medicine administration tool, and also provides a test example to show a sterilization effect of the above-mentioned second production example of the water-absorbent carrier.

As illustrated in FIGS. 2A to 2D, a solid medicine such as a freezedried medicine or a powdered medicine is enclosed in a vial 62. A saline solution bag 63 is filled with a dissolution liquid of saline water in which the medicine is dissolved immediately before administration to be made injectable into a vein. A double head needle 61 made of resin is a member made of a synthetic resin and has, at both ends thereof, needle tips capable of penetrating a rubber plug or the like. The double head needle 61 can thus communicate with the insides of both containers. Owing to such communication, the dissolution liquid is introduced into the vial, where the solid medicine is dissolved in the saline solution bag 63. The liquid in which the medicine is dissolved is then returned to the dissolution liquid container. This operation is repeated several times if needed, whereby the medicine can be made available for administration.

Figure 3:
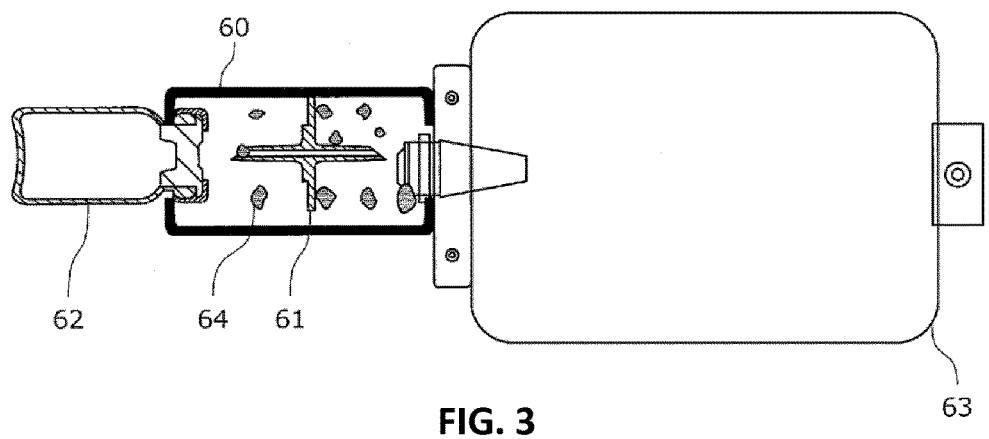
FIG. 3 is a view illustrating an example of using a water-absorbent carrier for the medicine administration tool (Example 6).

As illustrated in FIG. 3, the medicine administration tool is obtained by separately manufacturing the vial 62 in which aseptic powder processed using an aseptic technique is closely packaged and the saline solution bag 63 filled with an aseptic dissolution liquid, containing the double head needle 61 made of resin and a water-absorbent carrier 64 in a cylindrical member 60 with both ends thereof opened, and arranging the cylindrical member 60 between the vial 62 and the saline solution bag 63. The cylindrical member 60 is flexible, and connected to the vial 62 and the saline solution bag 63 so that the inside of the cylindrical member 60 is closely sealed. In addition, 10 granules of the water-absorbent carrier 64 (second production example) produced in Example 2 are enclosed in the sealed space within the flexible cylindrical member 60.

Then, by using, for example, two dryers, hot air at 120° C. is blown to only the cylindrical member 60 by one dryer so that the cylindrical member 60 is heated for 15 minutes, while cold air is blown to the vial 62 by the other dryer so as to prevent the temperature of the vial 62 from increasing and protect the medicine. After that, the heated cylindrical member 60 is left to cool, so that a kit product for medicine dissolution is obtained.

In order to confirm a sterilization property in the present Example, a filter paper to which 6th power CFU of *Geobacillus stearothermophilus* was attached was added as the BI to the above-mentioned manufacturing step operation together with the water-absorbent carrier. Such a medicine administration tool was then assembled and set, so that the kit product was obtained. After that, the BI was taken out and put in a medium. As a result, bacteria were not observed, and the successful sterilization was confirmed.

EXAMPLE 7

Example of Using Water-Absorbent Carrier for Bag-Shaped Container (Test Example)

Example 7 is an example of using the water-absorbent carrier for a bag-shaped container, and also provides a test example to show a sterilization effect of the above-mentioned first production example of the water-absorbent carrier.

Figures 4A, 4B:
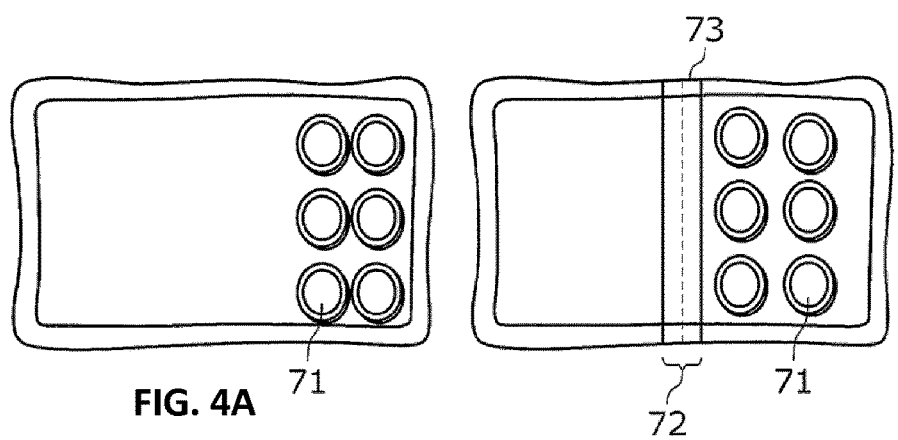
FIGS. 4A and 4B are views illustrating an example of using a water-absorbent carrier for a bag-shaped container (Example 7).

It is illustrated in FIG. 4A that six water-absorbent carriers 71 (first production example) in Example 1 are housed in the closable bag-shaped container produced using an OPP/CPP film. A medical device (not illustrated) which needs to be sterilized is housed in the bag-shaped container. The inside of the bag-shaped container in that state is heated at 121° C. for 20 minutes, so that the inside of the bag-shaped container can undergo the moist heat sterilization (moist heat sterilization). Since water vapor and water after the sterilization are absorbed into the water-absorbent carriers 71, the inside of the closed bag-shaped container is free from excess water.

FIG. 4B is an example illustrating that a portion containing the water-absorbent carriers 71 can be separated from the closed bag-shaped container at a seal portion 72 set as a boundary. Specifically, the seal portion 72 is produced, for example, by heat after the sterilization is completed. The portion containing the water-absorbent carriers 71 is then separated at a cutoff line 73 disposed on the seal portion 72, whereby a closed bag in which the medical device is contained can be provided.

Such a bag-shaped container can be utilized as a container for a tissue or an organ separated from a human.

EXAMPLE 8

Example of Using Water-Absorbent Carrier for Two-Chamber Prefilled Syringe (Test Example)

Example 8 is an example of using the water-absorbent carrier for a two-chamber prefilled syringe, and also provides a test example to show a sterilization effect of the above-mentioned third production example of the water-absorbent carrier.

Figure 5:
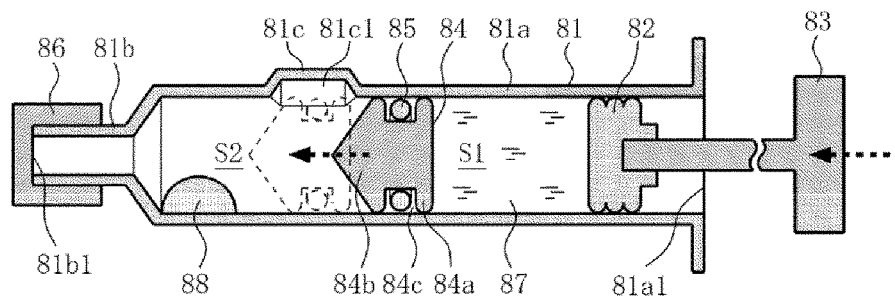
FIG. 5 is a view illustrating an example of using a water-absorbent carrier for a two-chamber prefilled syringe (Example 8).

As illustrated in FIG. 5, the two-chamber prefilled syringe 81 continuously includes a barrel 81a and a nozzle 81b. The barrel 81a has an opening 81a1 at the right end of the drawing, and the nozzle 81b has an opening 81b1 at the left end of the drawing. In addition, on the barrel 81a at the left side of the center of the drawing, a portion 81c for securing a bypass passage 81c1 at an inner side of the portion 81c is formed on at least a part of an outer periphery. A first gasket 82 is arranged at the right side of the drawing within the barrel 81a, and a plunger 83 is connected to the first gasket 82. Furthermore, a second gasket 84 is arranged substantially at the center of the drawing within the barrel 81a, and a water-absorbent carrier 85 in an O-ring shape is arranged around the second gasket 84. Specifically, the second gasket 84 has an annular recessed part 84c between a disk-shaped part 84a and a conical part 84b, and the water-absorbent carrier 85 in the O-ring shape is mounted on the annular recessed part 84c.

Hereinafter, a method for producing the water-absorbent carrier 85 in the O-ring shape conforming to the above-mentioned third production example will be described. First, the following materials are prepared.

water-absorbent substance: zeolite 4A (Tosoh Corporation)

synthetic resin: silicone elastomer, 10% toluene dispersion liquid of 1:1 mixture of A component and B component of Medical Grade ETR Elastomer Q7-4750 (Dow Corning Corp.)

In addition, a mold made of stainless steel having an annular groove corresponding to the water-absorbent carrier in the O-ring shape is also prepared.

Next, the water-absorbent substance is put in the annular groove of the mold, and the synthetic resin is poured onto the water-absorbent substance. The synthetic resin and the water-absorbent substance are prepared such that the resin is 4 pts.wt., expressed in terms of dried weight, to 1 pts.wt. of the water-absorbent substance. The toluene is then volatilized to produce a molded object (water-absorbent carrier) in the O-ring shape within the annular groove (bottom part) of the mold.

The produced water-absorbent carrier in the O-ring shape was left as it was in a desiccator containing a saturated solution of salt for 3 days, and water was carried on the water-absorbent carrier until water absorbency of the water-absorbent carrier reached its upper limit. As a result, the weight increased by the equivalent of 22% of the weight of the zeolite. In other words, it has been clarified that the water absorbency of the water-absorbent carrier is 22%. In addition, since a water carrying amount of the zeolite used for manufacturing the water-absorbent carrier is equivalent, at 100° C., to 10% of the weight of the zeolite, the water carrying amount in this case was set to 15%. Based on the above, the produced water-absorbent carrier in the O-ring shape was put in a desiccator together with water equivalent to 15% of the weight of the water-absorbent carrier, so that the water-absorbent carrier in the O-ring shape having a water carrying amount of 15% was obtained.

For the test, the two-chamber prefilled syringe 81 made of glass having a capacity of 5 mL is prepared. The water-absorbent carrier 85 in the O-ring shape produced in the above-mentioned way is mounted on the annular recessed part 84c of the second gasket 84 made of butyl rubber. Next, the second gasket 84 on which the water-absorbent carrier 85 in the O-ring shape is mounted is pushed into the barrel 81a from the opening 81a1 to be positioned substantially at the center of the drawing within the barrel 81a. Then, water for dissolution (refer to reference sign 87) is put in a chamber S1 at the rear side of the second gasket 84 in the drawing. After that, the first gasket 82 made of butyl rubber is pushed into the barrel 81a from the opening 81a1 to seal the two-chamber prefilled syringe 81. The two-chamber prefilled syringe 81 in that state is subjected to the autoclave process at 121° C. for 20 minutes to be sterilized. After the sterilized syringe 81 is dried, 1 g of glucose powder (refer to reference sign 88) is put in a chamber S2 at the front side of the second gasket 84 in the drawing through the opening 81b1. The opening 81b1 is then closed with a cap 86 made of butyl rubber. An example product was thus obtained.

Meanwhile, another syringe was also produced in the same way as described above except that the water-absorbent carrier 85 in the O-ring shape was not mounted on the annular recessed part 84c of the second gasket 84. A comparative product was thus obtained.

The above-mentioned example product and comparative product were stored at 40° C. and 75% RH for 3 months, and a water amount of the glucose 88 within the front side chamber S2 was measured for each product. As a result, it was confirmed that the example product had a water amount of 1.3%, which was substantially the same as its initial value 1.2%. On the other hand, the comparative product stored for 3 months had a water amount of 4.3% with respect to its initial value 1.2%.

In order to confirm a sterilization property, a filter paper to which $10^6$ CFU/support of *Geobacillus stearothermophilus* was attached was put as the BI in the annular recessed part 84c of each of the above-mentioned example product and comparative product. As a result, propagation of bacteria was not observed in the example product while propagation of bacteria was observed in the comparative product.

Therefore, it has been revealed that the water-absorbent carrier 85 in the O-ring shape not only provides water as a sterilant during the sterilization but also absorbs, when stored for a long time, water that tries to infiltrate the front side chamber S2 from the rear side chamber S1 to maintain a dry condition and quality of the glucose 88. According to this result, it can be understood that the two-chamber prefilled syringe according to the present invention is useful as a two-chamber prefilled syringe in which a biological medicine having a risk of water deterioration is contained.

Incidentally, the above-mentioned example product is the two-chamber prefilled syringe which is used in the following way. In the state of FIG. 5, the injection needle, a tube (not illustrated) or the like is connected to the nozzle 81c after the cap 86 is removed. The plunger 83 is then pushed to the left side of the drawing (refer to dashed arrow) to move the first gasket 82 to the left side of the drawing. This movement causes, via the water for dissolution 87, the second gasket 84 to move to the left side of the drawing (refer to dashed arrow). When the second gasket 84 moves to the left side of the drawing to reach a position indicated by a dashed line, the water for dissolution within the rear side chamber S1 flows into the front side chamber S2 through the bypass passage 81c1. The liquid (medicine) in which the glucose 88 is dissolved then flows out through the injection needle, the tube or the like. During the sterilization of the water for dissolution, sufficient moist heat is supplied, from the water-absorbent carrier 85, to a region including surfaces of the annular recessed part, the barrel surrounding the annular recessed part, and the gasket, whereby such a region is sterilized. Therefore, this operation, when performed, can prevent bacteria from being brought, from such a region, into the water for dissolution 87 and the dissolved liquid, and from contaminating the water for dissolution 87 and the dissolved liquid.

<<Working of Present Invention>>

The present invention has successfully provided the water-absorbent carrier obtained by embedding the water-absorbent substance in the synthetic resin. An object of the water-absorbent substance is to evaporate water carried thereon as water vapor when heated, and absorb the released water when cooled. Therefore, the present invention works so as not to generate foreign matter and deteriorate a function of the medical article even in a narrow space, and works so that the sterilant (water vapor) for the moist heat sterilization reaches a desired space.

Since the void is provided between the water-absorbent substance and the synthetic resin, the water-absorbent substance can exhibit its water-absorbing property without being inhibited.

In addition, since the present invention has successfully provided such a manufacturing method that the water-absorbent resin is embedded in the synthetic resin so that the synthetic resin does not enter an inner hole part of the water-absorbent carrier, the water-absorbent carrier has become manufacturable.

Since the present invention has successfully provided the sterilization method for subjecting a space that vapor cannot readily enter to the moist heat sterilization, the present invention works so that the medical article packaged in a closed space (i.e. inside of the bag-shaped container) to be sterilized can be provided.

INDUSTRIAL APPLICABILITY

The present invention can be applied to a water-absorbent carrier for moist heat sterilization which can be used even in a narrow space, does not generate foreign matter, and does not deteriorate a function of a medical article, a method for manufacturing the water-absorbent carrier, the medical article, and a moist heat sterilization method.

REFERENCE SIGNS LIST 51 first shaft
52 first spacer
53 water-absorbent carrier
54 second spacer
55 second shaft
61 double head needle
62 vial
63 disposal saline solution bag
64 water-absorbent carrier
71 water-absorbent carrier
72 seal portion
73 cutoff line
81 two-chamber prefilled syringe
81a barrel
81b nozzle
81c1 bypass passage
82 first gasket
83 plunger
84 second gasket
85 water-absorbent carrier in O-ring shape
86 cap

The invention claimed is:

1. A method for manufacturing a water-absorbent carrier, comprising:
   immersing a water-absorbent substance in an aqueous solution in which a water-soluble substance is dissolved to impregnate the water-absorbent substance with the water-soluble substance;
   drying the water-absorbent substance impregnated with the water-soluble substance;
   embedding the dried water-absorbent substance impregnated with the water-soluble substance in a thermoplastic synthetic resin to obtain a molded body; and
   washing the molded body to remove the water-soluble substance.

2. The method for manufacturing a water-absorbent carrier according to claim 1, wherein
   the dried water-absorbent substance impregnated with the water-soluble substance is embedded in the thermoplastic synthetic resin in such a way that while the thermoplastic synthetic resin is heated and dissolved, the thermoplastic synthetic resin is mixed with the water-absorbent substance, and then cooled.

* * * * *